United States Patent
Rüegg et al.

[11] Patent Number: 6,142,022
[45] Date of Patent: Nov. 7, 2000

[54] PROCESS AND DEVICE FOR WEAR TESTING ON A PRESSING CLAMP

[75] Inventors: Urs Rüegg, Rapperswil; Matthias Friedli, Forch, both of Switzerland

[73] Assignee: Geberit Technik AG, Jona, Switzerland

[21] Appl. No.: 09/170,600

[22] Filed: Oct. 13, 1998

[30] Foreign Application Priority Data

Oct. 13, 1997 [CH] Switzerland ............... 2388/97

[51] Int. Cl.[7] .................................................. G01N 3/08
[52] U.S. Cl. .................................................. 73/821; 73/851
[58] Field of Search .................. 73/818, 821, 823, 73/849, 851, 853, 854, 856, 859, 860

[56] References Cited

U.S. PATENT DOCUMENTS

| | | | |
|---|---|---|---|
| 306,730 | 10/1884 | Emery | 73/859 |
| 3,461,715 | 8/1969 | Stover | 73/818 |
| 5,459,676 | 10/1995 | Livingston | 364/528.31 |
| 5,459,767 | 10/1995 | Lessing | 376/245 |
| 5,567,870 | 10/1996 | Harris | 73/81 |
| 5,945,607 | 8/1999 | Peppel et al. | 73/856 |

FOREIGN PATENT DOCUMENTS

| | | |
|---|---|---|
| 296 02 238 U1 | 5/1996 | Germany . |
| 296 04 276 U1 | 5/1996 | Germany . |
| 687 368 A5 | 11/1996 | Switzerland . |

*Primary Examiner*—Max Noori

[57] ABSTRACT

A test body is compressed a reference measure in the wear test on compression pincers. The test body is compressed preferably between two compression jaws. The test body is a bolt which is compressed to become flat, with at least one volumetric measure, preferably a thickness measure, of the compressed bolt serving as the reference measure of the prevailing test force. The process facilitates simple and dependable wear testing, even at building sites.

14 Claims, 2 Drawing Sheets

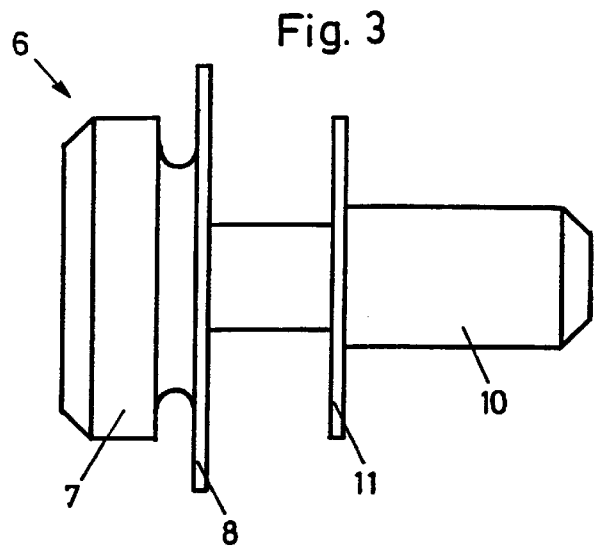
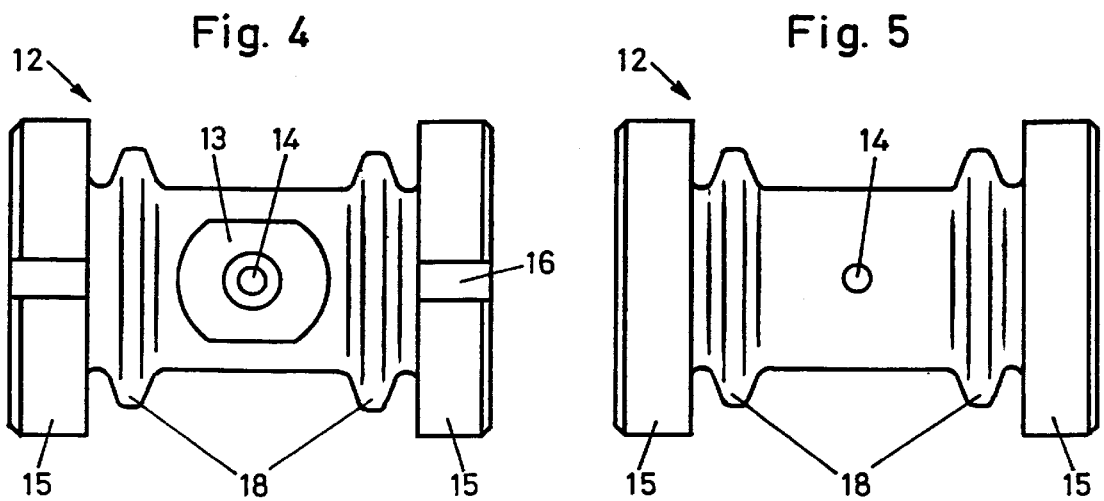
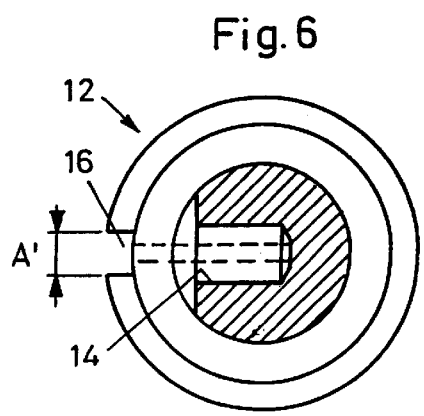

PROCESS AND DEVICE FOR WEAR TESTING ON A PRESSING CLAMP

TECHNICAL FIELD

The invention relates to a process for the wear test on compression pincers having at least two compression jaws which can be moved toward each other to form a substantially closed compression compartment.

BACKGROUND OF THE INVENTION

Applicant's CH-A-687 368 discloses compression pincers for producing tube joints. Those compression pincers have two compression levers which are adapted to swivel in opposite directions and are provided with a jaw having a mouthlike recess for accommodating the tip of a tube or of a press socket. These compression levers are connected to pincer drive means with which the compression levers can be swivelled for closing the jaws. These and similar compression pincers have been used for a long time for installing water tubing.

In regard to ensure complete sealing of such tube connections, it has been known that such compression pincers experience inevitable wear and that periodic testing is mandatory.

In DE-0-296 02 238 for the wear test there has been proposed a test instrument having a gap-width detector with which the width of the gap between opposite faces of two adjacent compression jaws can be measured. The gap-width detector is configured as an optical sensor with a laser and a receiver of light.

An other test instrument has been known from DE-0-296 04 276. The limit force of the drive means of the tool are checked with this test instrument. This instrument has an electronically controlled linear valve with which the force/path-of-travel characteristic of the drive means is simulated.

The two aforementioned test instruments are comparatively expensive and the test procedure Is laborious. As a rule, these test instruments cannot be used on a building site.

SUMMARY OF THE INVENTION

The problem underlying the invention is to provide a process and a device for the wear test on compression pincers, which process and device are substantially simpler and less expensive and also facilitate the use on building sites.

The process according to the invention is characterised in that a test body is compressed as a reference means of the prevailing test force. The compression of such a test body is without problems possible on a building site. Thus, an expensive test instrument which is laborious in regard to maintenance and operation is avoided. It is an important aspect that both the drive means and the compression jaws can be tested simultaneously via the compression of the test body. In this way wear effects or defects of the drive means, as well as of the compression jaws, can be found.

The test body is compressed preferably between two compression jaws. In principle, the test body can be compressed also at some other point of the compression pincers, e.g., between the compression lever and the drive means.

The process is particularly simple and safe whenever, in accordance with an other embodiment of the invention, the test body is a bolt which is compressed to become flat. A volumetric measure of the compressed bolt in this case can be used as the reference indication of the compression force applied. The thickness of the compressed part is preferably used as a volumetric measure.

The accuracy of the method is particularly high if, in accordance with an other embodiment of the invention, a holder for the test body is inserted into the compression pincers for the purpose of positioning the test body. The holder ensures that the test bodies upon compression always assume the same, predetermined relative position. The manipulation is particularly simple if the holder is placed between two compression jaws and is provided with a bore into which the test body is inserted. Such a holder can be used repeatedly for compression. The holder, and also the test bodies, require but little space and therefore can be easily carried in a tool box to a building site.

The test body is preferably made from metal, specifically from a light metal alloy. A test body made from Anticorodal 112 facilitates particularly accurate testing.

The device according to the invention has a test body which can undergo plastic deformation and is to be compressed in the compression pincers as a reference measure of the prevailing compression force. According to an other embodiment of the invention, the test body is a bolt having a head and a shaft. The shaft serves for positioning the bolt and the head is deformed in the test operation. The head is deformed preferably between the front faces of the compression jaws. In this operation, the shaft protrudes into the mouth-like recess in the compression jaws and is preferably positioned within a holder.

According to a further embodiment of the invention, the holder comprises means for checking the deformed test body. These means can have the form of a slit with a well-defined width. If the deformed part can be inserted into the slit, it has been shown that the compression jaws reach the required limit force. If the deformed part is too wide and therefore cannot be inserted into the slit, the device does not reach the required compression force. Wear at the compression pincers or a defect of the drive means may be the reason. In this case, the compression pincers naturally must not be used.

Other advantageous features are obvious from the dependent claims, the following description, and the drawing.

BRIEF DESCRIPTION OF THE DRAWINGS

An embodiment of the invention is described below in greater detail by way of the drawing. There show:

FIG. 3, an enlarged-scale view of the test body;

FIG. 4, a view of a holder;

FIG. 5, an other view of a holder according to FIG. 4; and

FIG. 6, a cross section of a holder.

DETAILED DESCRIPTION OF THE PREFERRED EMBODIMENT

Figure 1:
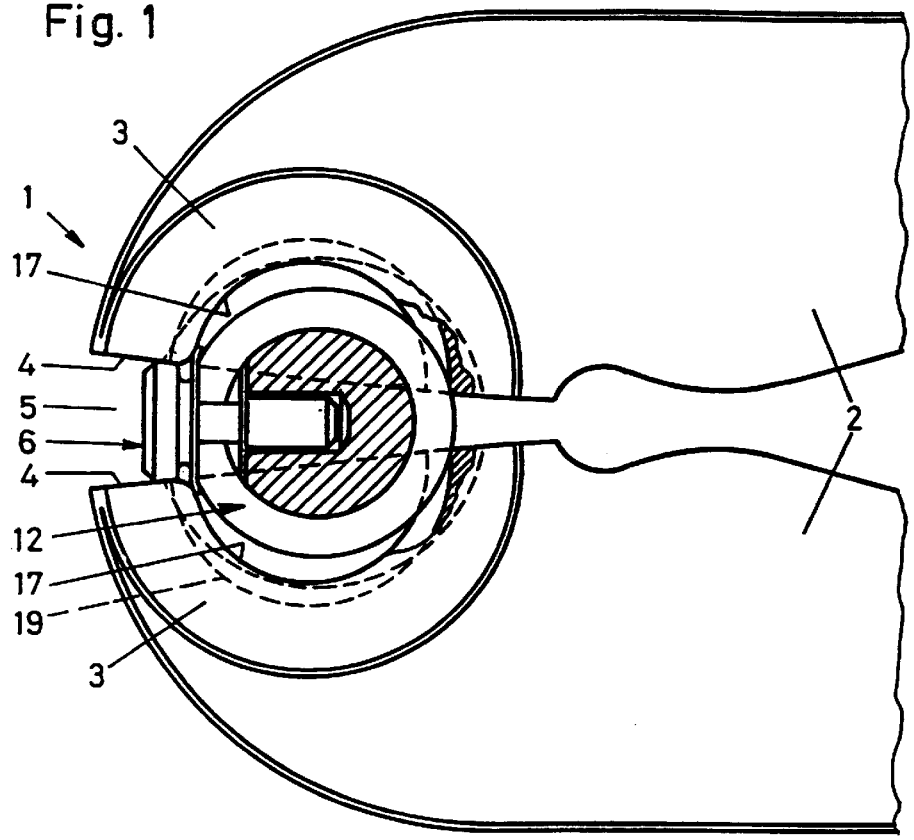
FIG. 1, a partial view of compression pincers with an inserted test body in full view and the cross section of a holder.
Figure 2:
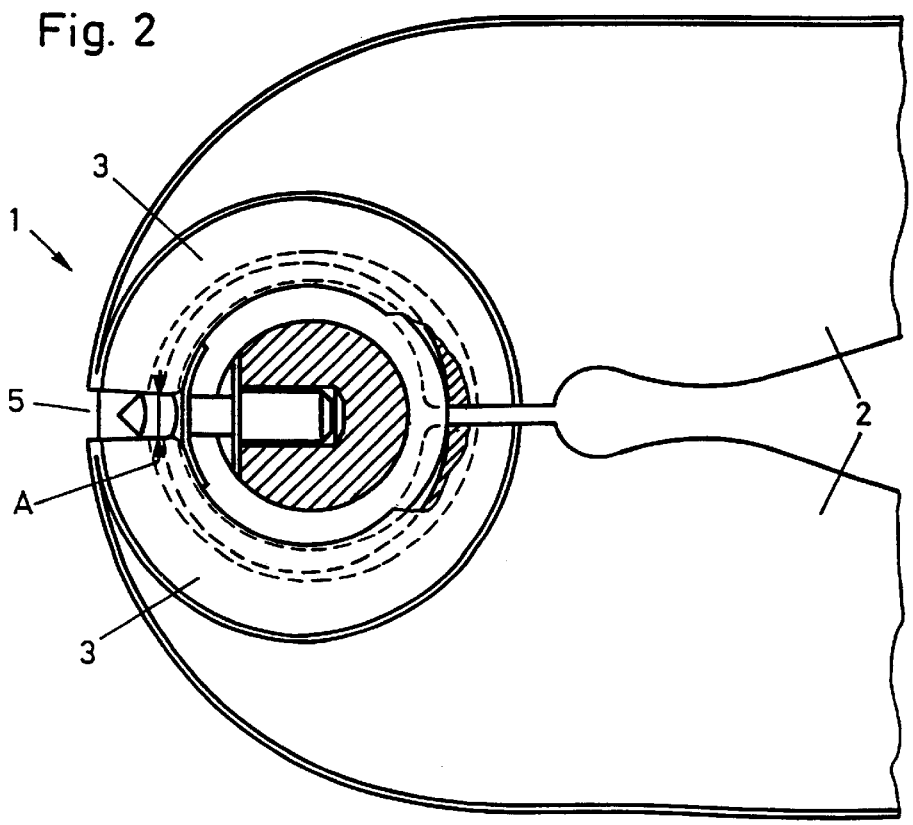
FIG. 2, a view as in FIG. 1 but after compression of the test body.

The compression pincers 1 shown in FIGS. 1 and 2 correspond to the compression pincers disclosed in CH-A-687 368. Since the same are known per se, only the front ends of the two compression levers 2 are illustrated in FIGS. 1 and 2. Each of these compression levers 2 bears a compression jaw 3 with a front face 4 and a mouth-like recess 17. Between the two front faces 4 there is a gap 5 which is reduced to the gap shown in FIG. 2 when the two compression levers 2 are turned.

In order to verify the prevailing test force, there is provided a test body 6 which is adapted to be inserted by means of a holder 12 between the jaws 3, as shown in FIG. 1. The test body 6 is configured as a bolt with a length of, for example, 20 mm and made from a plastics material. Anticorodal 112 is particularly suitable as material. But also some other alloy can be contemplated. As shown in FIG. 3, the test body 6 has a head 7 which, as shown in FIG. 1, is positioned with the aid of the holder 12 between the two jaws 3 so that the test body is in a precisely predetermined position between the front faces 4 within the gap 5. The test body 6 is applied to the holder 12, with a shaft 10 engaging a matching bore 14. A comparatively thin disk 11 moulded onto the shaft 10 bears against a flat section 13. Thus, the disk 11 defines the depth to which the test body 6 can be inserted at the holder 12. As a further aid for the accurate positioning of the test body 6, the same has a collar 8 spaced from the head 7, with the collar 8-bearing on the inside of the jaws 3, as shown in FIG. 1. Thus, the position of the head 6 within the gap 5 is precisely defined by the holder 12 and the collar 8. According to FIGS. 4 and 5, the holder 12 is configured to match the recess 17. Circumferential elevations 18 therefore match corresponding hollows in the recess 17. Both the test body 6 and the holder 12 can be produced at low cost as lathe-turned parts. The test procedure is explained below.

In order to test the compression pincers 1 for the prevailing compression force, the holder 12 with an applied test body 6 is inserted between the opened jaws 3 as shown in FIG. 12. The two compression levers 2 are swivelled with the drive means (not illustrated) as in the case of the compression of a tube. In place of a tube, now the test body 6 is compressed at its head 7. Upon compression, the collar 8 is applied to the inside of the recess 17 and deformed thereby, as clearly shown in FIG. 2. The collar 8 prevents the head 7 from moving radially outwards in the slit 5 during the compression.

FIG. 2 shows the two compression jaws 2 after termination of the compression process. As indicated, the slit 5 is much narrower than before the compression and the head 7 has been plastically deformed to a plate-shaped part of thickness A. The thickness A is a measure of the width of the gap 5. The thickness A is also a measure of the final force reached. In the case of wear at the compression pincers 1 or of a defect of the drive means, the stipulated final force is not reached and the thickness A is accordingly larger than a preset measure.

After the compression, the compression pincers 1 are released and, after opening the two jaws 3, the compressed test body 6, together with the holder 12, can be removed from the compression pincers. As shown in FIGS. 4 and 6, the holder 12 has a slit 16 at each of its lateral flanks 15 for the purpose of checking the test body. These slits have a width A' which is only slightly greater than the thickness A. If the compressed head 7 can be inserted into one of the slits 16, it can be assumed that the prevailing test force is adequate. If this cannot be done, the thickness A is greater than the gap width A' and then it must be assumed that the compression pincers 1 cannot reach the required test force. The compression pincers 1 therefore must be checked for wear which might have occurred or for defective drive means and must be retested or replaced. The compressed test body 6 can be dispatched together with it as evidence.

The holder 12 can be reused for further testing of the compression force. Only the test body 6 has to be replaced by a new one. Such test bodies 6 can be produced at very low cost as a lathe-turned part. Thus, the wear test with the aid of the test body 6 is very inexpensive and simple and can be carried out rapidly. Specialised knowledge or particular tradesman skills are not required. The test body and the holder can be accommodated in a small space within any tool box. Therefore the wear test with the device according to the invention can be carried out without problems at the building site proper. Since the costs are low and the time required is short, more frequent testing than in the past is now possible at low expenses. Thus, more reliably than in the past, insufficient compression of joints is avoided. Very expensive structural damage resulting from non-sealing joints can be prevented in a very reliable fashion.

What is claimed is:

1. A process for the wear test on a compression pincer having at least two compression jaws which are adapted to be moved toward each other to form a substantially closed compression compartment wherein a test body is used as a reference means for the prevailing test force, wherein the test body is a bolt which is compressed to become flat and that at least one volumetric measure of the compressed bolt is used as the reference measure of the prevailing compression force.

2. The process according to claim 1 wherein the test body is compressed between two compression jaws.

3. The process according to claim 1 wherein during the compression, the test body is supported by a shaft molded to the test body and positioned in place.

4. The process according to claim 1 wherein the test body is inserted into a holder for the purpose of positioning the test body relative to the compression jaws.

5. The process according to claim 4 wherein the holder is placed between the at least two compression jaws.

6. A device for the wear test on a compression pincer having at least two compression jaws which are adapted to be moved toward each other to form a substantially closed compression compartment, wherein the device comprises
   a test body which is
      receivable in the compression pincer and
      plastically deformable by the compression pincer to form a flat in the test body,
   such that a volumetric measure the test body at the flat preferably a thickness, provides a reference measure of the prevailing compression force.

7. The device according to claim 6 wherein the device comprises a holder for positioning the test body.

8. The device according to claim 6 wherein at least one section of the test body is compressed between two faces of the two compression jaws.

9. The device according to claim 6 wherein the test body is configured as a bolt having a head and a shaft.

10. The device according to claim 7 wherein the holder is adapted to be inserted between the two compression jaws.

11. The device according to claim 10 wherein the holder has at least one slit for receiving and checking the compressed test body.

12. The device according to claim 6 wherein the test body is made from metal.

13. The device according to claim 7 wherein the test body has a head and a collar for positioning the head.

14. The device according to claim 7 wherein the test body has a disk arranged at the shaft for the purpose of positioning the test body at the holder.

* * * * *